US009615892B2

(12) United States Patent
Piferi et al.

(10) Patent No.: US 9,615,892 B2
(45) Date of Patent: Apr. 11, 2017

(54) SURGICAL DRAPES WITH PATCHES TO PROVIDE PORTS

(75) Inventors: Peter Piferi, Orange, CA (US); Carol Barbre, Orange, CA (US)

(73) Assignee: MRI INTERVENTIONS, INC., Memphis, TN (US)

( * ) Notice: Subject to any disclaimer, the term of this patent is extended or adjusted under 35 U.S.C. 154(b) by 2132 days.

(21) Appl. No.: 12/631,300

(22) Filed: Dec. 4, 2009

(65) Prior Publication Data
US 2010/0139669 A1 Jun. 10, 2010

Related U.S. Application Data

(60) Provisional application No. 61/119,837, filed on Dec. 4, 2008.

(51) Int. Cl.
*A61B 19/10* (2006.01)
*A61B 46/23* (2016.01)

(52) U.S. Cl.
CPC .................................. *A61B 46/23* (2016.02)

(58) Field of Classification Search
CPC ..... A61B 19/081; A61B 19/088; A61B 19/10; A61B 2019/081; A61B 2019/082; A61B 2019/10; A61B 2019/103
USPC .......... 128/849–856; 604/355–357; 600/119, 600/121–125
See application file for complete search history.

(56) References Cited

U.S. PATENT DOCUMENTS

| 3,882,859 | A | * | 5/1975 | Ericson ......................... 128/854 |
| 3,916,447 | A | | 11/1975 | Thompson |
| 3,968,792 | A | | 7/1976 | Small |
| 4,196,723 | A | * | 4/1980 | Moose, Jr. .................... 128/854 |
| 4,323,062 | A | * | 4/1982 | Canty .......................... 128/852 |
| 4,553,539 | A | * | 11/1985 | Morris ......................... 128/854 |
| 4,998,538 | A | | 3/1991 | Charowsky et al. |
| 5,275,177 | A | | 1/1994 | Wilk |
| 5,312,385 | A | | 5/1994 | Greco |
| 5,345,946 | A | * | 9/1994 | Butterworth et al. ........ 128/853 |
| 5,653,938 | A | | 8/1997 | Faries, Jr. et al. |
| 6,093,182 | A | * | 7/2000 | Lampropoulos et al. .... 604/533 |
| 6,102,044 | A | | 8/2000 | Naidyhorski |
| 6,123,080 | A | | 9/2000 | Mohan et al. |
| 6,400,979 | B1 | | 6/2002 | Stoianovici et al. |
| 6,456,684 | B1 | | 9/2002 | Mun et al. |
| 6,762,606 | B2 | | 7/2004 | Jevtic et al. |

(Continued)

FOREIGN PATENT DOCUMENTS

KR 10-2000-0035938 A 6/2000
KR 10-0330106 B1 8/2002

(Continued)

OTHER PUBLICATIONS

Merriam-Webster, Preferentially-Definition, accessed from www.merriam-webster.com on Mar. 6, 2013.*

(Continued)

*Primary Examiner* — Kari Petrik
(74) *Attorney, Agent, or Firm* — Myers Bigel, P.A.

(57) ABSTRACT

Surgical drapes having opposing first and second primary surfaces with fixably attachable patches to provide ports through which cables or tools can be inserted without compromising a sterile field. The patches may be earlier affixed to the surgical drape or the patch may be affixed in situ by a clinician to the drape prior to a surgical procedure.

16 Claims, 16 Drawing Sheets

(56) References Cited

U.S. PATENT DOCUMENTS

| | | |
|---|---|---|
| 6,916,301 B1 | 7/2005 | Clare |
| 6,939,296 B2 * | 9/2005 | Ewers et al. .................. 600/206 |
| 7,537,564 B2 | 5/2009 | Bonadio et al. |
| 2003/0181810 A1 | 9/2003 | Murphy et al. |
| 2005/0145254 A1 * | 7/2005 | Aboul-Hosn et al. ........ 128/849 |
| 2007/0113859 A1 * | 5/2007 | Allen et al. .................. 128/853 |
| 2008/0216844 A1 | 9/2008 | Olfert et al. |

FOREIGN PATENT DOCUMENTS

| | | |
|---|---|---|
| KR | 10-0516288 | 9/2005 |
| KR | 10-2008-0085138 A | 9/2008 |
| KR | 20-0441909 Y1 | 9/2008 |
| WO | WO 2007-108771 A1 | 9/2007 |

OTHER PUBLICATIONS

Notification of Transmittal of the International Search Report and the Written Opinion of the International Searching Authority, or the Declaration, PCT/US2009/066762, Jul. 20, 2010, 12 pages.
Notification concerning transmittal of international preliminary report on patentability for PCT/US2009/066762 mailed Jun. 16, 2011.

* cited by examiner

# SURGICAL DRAPES WITH PATCHES TO PROVIDE PORTS

RELATED APPLICATIONS

This application claims priority from U.S. Provisional Application No. 61/119,837, filed Dec. 4, 2008, the disclosure of which is hereby incorporated herein in its entirety.

BACKGROUND OF THE INVENTION

Surgical drapes are used to cover a patient during an operative procedure. They are generally constructed of a material that is impervious to blood and other bodily fluids. In this regard, surgical drapes may attempt to provide a sterile field on the clinician side. However, sometimes a surgical drape is cut or slit to provide an aperture or fenestration at the operative site. Such openings can compromise the sterility of the drape on the clinician side, particularly if they are larger than necessary for the operative procedure.

Surgical drapes have been used to preserve a sterile field or environment in Magnetic Resonance Imaging (MRI) interventional brain surgery procedures. Often in these procedures, opening(s) in the surgical drape need to be made to accommodate a cable or set of cables. Pre-cut openings or openings cut sua sponte in surgical drapes may be larger than necessary, thereby compromising the sterile field on the clinician side.

SUMMARY OF EMBODIMENTS OF THE INVENTION

In view of the above, embodiments of the invention provide surgical drapes with patches and/or patches for surgical drapes and methods for using the same, as well as related medical kits.

Some embodiments are directed to surgical drapes. The surgical drapes include first and second opposing primary surfaces. At least one patch having first and second opposing primary surfaces is fixably attached to the surgical drape and overlies an aperture in the surgical drape. The at least one patch defines a through-port thereby allowing at least one cable, tool, or instrument to extend snugly therethrough.

In some embodiments, the at least one patch is preferentially scored to allow the at least one cable, tool, or instrument to extend therethrough. In some embodiments, either the first or the second opposing primary surface of the at least one patch includes an adhesive to fixably attach the patch to one of the opposing primary surfaces of the surgical drape. At least one of the opposing first and second primary surfaces of the at least one patch may include a first inner portion and a second outer perimeter portion wherein only the second outer perimeter portion includes the adhesive. The at least one patch further may further include a releasable cover overlying the adhesive.

Yet other embodiments are directed to methods of introducing a cable, tool or instrument having first and second opposite end portions into a surgical environment while maintaining a sterile field. The methods may include: (a) providing a surgical drape having first and second opposing primary surfaces, wherein the first primary surface defines a sterile side and the second primary surface defines a non-sterile side, and wherein at least one patch is fixably attached to the first primary surface; and (b) passing the first end portion of the cable, tool or instrument through the at least one patch so that the second end portion resides on the sterile side of the surgical drape and the first end portion resides on the non-sterile side of the surgical drape, wherein the cable, tool or instrument is snugly held by the at least one patch.

In some embodiments, the methods include fixably attaching the at least one patch in situ by a clinician to the sterile primary surface of the surgical drape prior to a surgical procedure before the providing step. In some embodiments, the methods include puncturing, slicing or piercing the at least one patch and/or the surgical drape with a sterile tool after the attaching step and before the passing step. The sterile tool may include a cap that is removably attached to the first end portion of the cable, tool or instrument. In some embodiments, the methods include positioning a coverlay at the first primary surface of the drape over the at least one patch and cable, tool, or instrument extended therethrough after the passing step.

Additional embodiments are directed to medical kits. The medical kits include at least one patch having opposing first and second primary surfaces, wherein the at least one patch is configured to be fixably attached to a surgical drape. The at least one patch is configured to define a port to allow at least one cable, tool or instrument to extend snugly therethrough. The at least one patch is packaged in a first sterile pouch.

In some embodiments, the medical kits include at least one sterile tool configured to puncture, slice or pierce the at least one patch. The at least one tool is packaged in a second sterile pouch, wherein both the first sterile pouch and the second sterile pouch are packaged in a third sterile pouch. The medical kits may include at least one cover having a first hollow piece connectable with a second hollow piece to enclose a respective sterile tool. The at least one cover is packaged in the second sterile pouch.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Figure 1A:
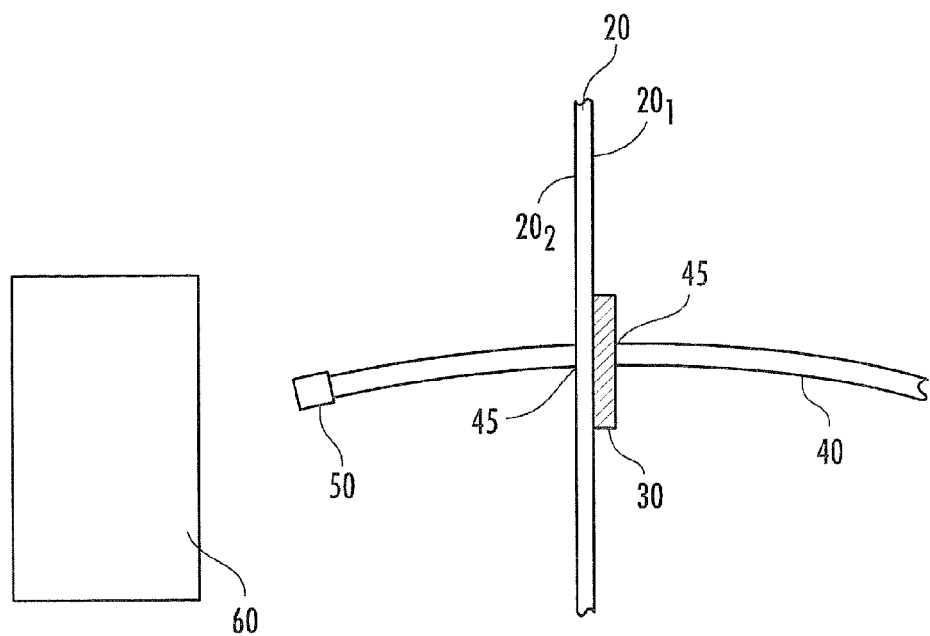
FIGS. 1A, 1B and 1C are side views of surgical drapes according to some embodiments of the present invention.

Further features, advantages and details of the present invention will be appreciated by those of ordinary skill in the art from a reading of the figures and the detailed description of the embodiments that follow, such description being merely illustrative of the present invention. Features shown with respect to one embodiment may be incorporated in other embodiments.

DETAILED DESCRIPTION OF EMBODIMENTS OF THE INVENTION

The present invention will now be described more fully hereinafter, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout.

In certain of the figures, the surgical drapes and patches illustrated herein have been noted to show a "rear" or "front" view for ease of discussion. However, these drapes and patches can be turned or alternatively configured to reflect the opposite view (e.g., instead of a front view, they can also show a rear view or instead of an outwardly facing surface they can show an inwardly facing surface). Also, although a feature is described with respect to one embodiment, this feature may be used with another embodiment.

Thicknesses and dimensions of some components may be exaggerated for clarity. Broken lines illustrate elements or features not visible from the presented view (e.g., on the opposite side) or as an optional element unless otherwise indicated. It will be understood that when an element is referred to as being "attached," "connected," or "coupled" to another element, it can be directly connected or coupled to the other element or intervening elements may be present. In contrast, when an element is referred to as being "directly attached," "directly connected," or "directly coupled" to another element, there are no intervening elements present.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "patch" (which can also be described as a grommet) refers to a component that can be attached to the surgical drape to provide a port, channel or aperture for a surgical tool, cable or other instrument or device. The patch can be of any suitable material, including a polymer, fabric, textile or a combination thereof and can provide increased structural rigidity to the surface of the surgical drape. The term "polymer" includes polymers, copolymers and derivatives thereof.

The term "sterile field" refers to an area or volume that can be created by placing a sterile surgical drape around a target surgical site to inhibit contamination. In this regard, the surgical drape may define an interface dividing a sterile field and a nonsterile field. Only sterile objects and personnel are typically allowed within a sterile field; once a sterile object within a sterile field comes in contact with a nonsterile object, the "sterile" object is no longer sterile. The term "sterile" means that the component meets surgical cleanliness standards and is typically substantially aseptic and/or substantially free from living germs or microorganisms.

Turning now to the figures, FIG. 1A illustrates a side view of an example of a surgical drape 20. The surgical drape 20 has opposing first and second primary surfaces $20_1$, $20_2$. The drape 20 also includes at least one patch 30. In the embodiment shown in FIG. 1A, a single patch 30 is configured to be fixably attached to one of the opposing primary surfaces $20_1$, $20_2$ of the surgical drape 20. As illustrated in FIG. 1A, the patch 30 is fixably attached to the first (inner) primary surface 20₁. The patch 30 may be alternatively attached to the second (outer) primary surface 20₂. The patch 30 is further configured to allow at least one surgical cable, tool or other instrument 40 to extend snugly therethrough. In this regard, the patch 30 can provide a channel/port 45. As shown in FIG. 1A, an end of the cable 40 that may extend through the channel/port 45 may include a connector 50, such as a BNC connector, for example. In other embodiments, shown in FIG. 1B, a patch 30 can reside on each of the opposing surfaces 20₁, 20₂ of the drape 20 to provide a channel/port 45.

Figure 1B:
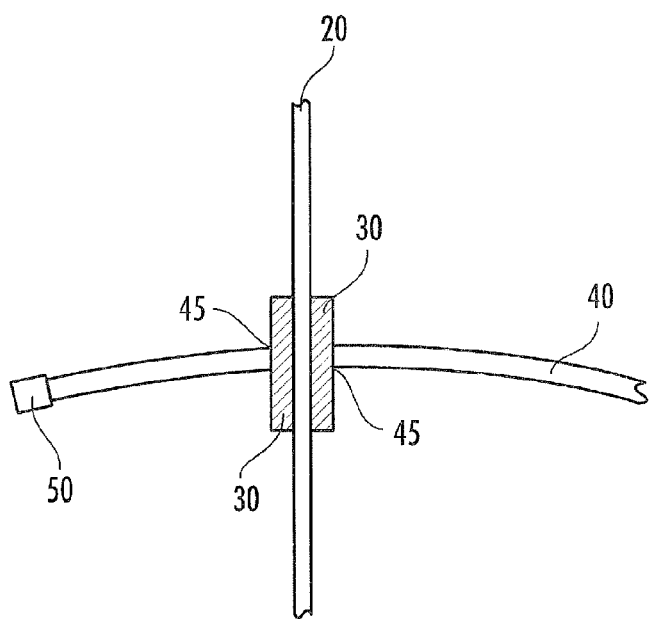
Figure 1C:
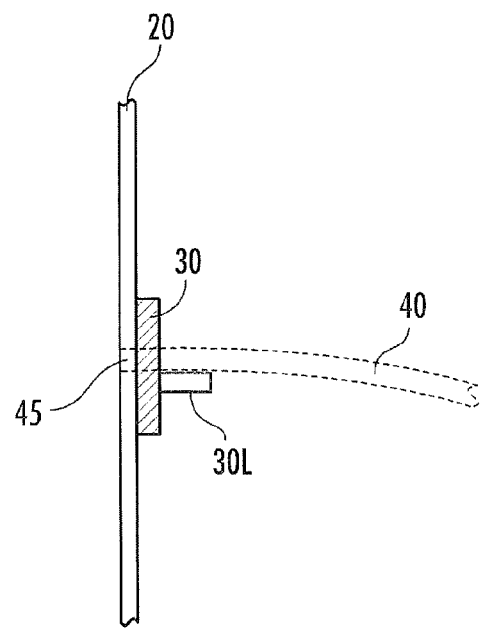
Figure 11:
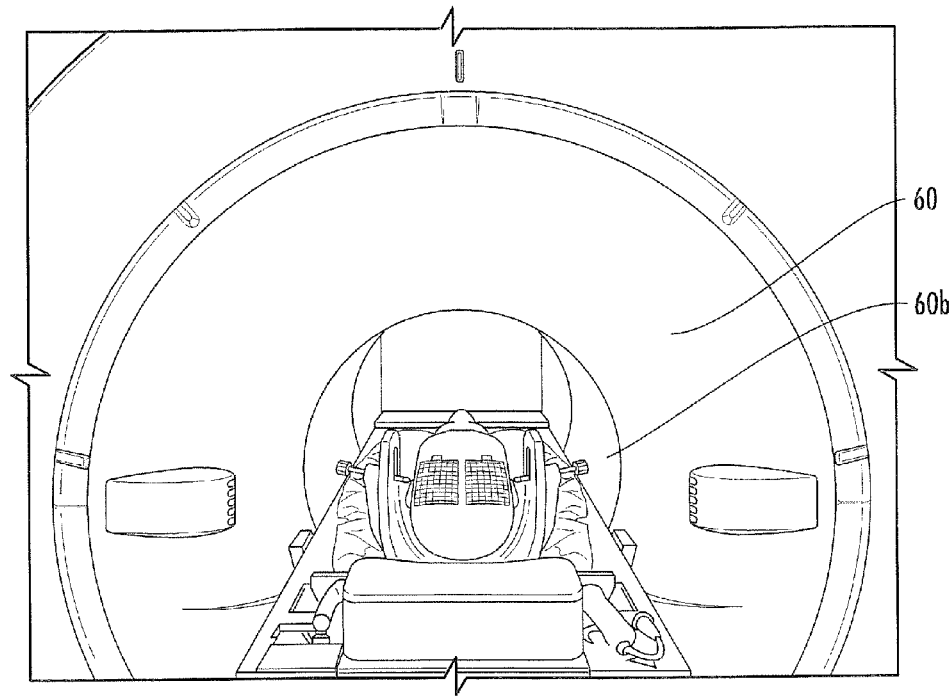
FIG. 11 illustrates a simulated patient situated within an MRI magnet housing defining a bore for MRI procedures.

FIG. 1C shows the patch 30 with a lip or ledge 30L that can provide additional support for the cable, tool or other instrument 40. The lip/ledge 30L can extend on a bottom portion of the patch as shown or may extend about a closed perimeter to allow the patch to be placed in different orientations.

Where used, the connector 50 (FIGS. 1A and 1B) can be configured to connect to an MRI compatible instrument, such as to a fiber optic camera probe or imaging coils. As exemplified in FIG. 11 and FIG. 12, the surgical drape 20 may attach to an MRI magnet housing 60 defining a bore 60b for MRI procedures. The drape can be suspended by hooks or loops at one end or both ends of the magnet housing. An exemplary MRI procedure involves intra-brain surgery and, in some particular embodiments, implantation of Deep Brain Stimulation (DBS) leads. DBS is becoming an acceptable therapeutic modality in neurosurgical treatment of patients suffering from chronic pain, Parkinson's disease or seizure, and other medical conditions. Embodiments of the present invention may also be suitable for a number of interventional procedures including, but not limited to, MRI-guided drug delivery procedures, MRI-guided ablation procedures, biopsies and the like for the brain and for other target sites including, for example, cardiac surgeries such as cardiac electrophysiology (EP) procedures.

Figure 2A:
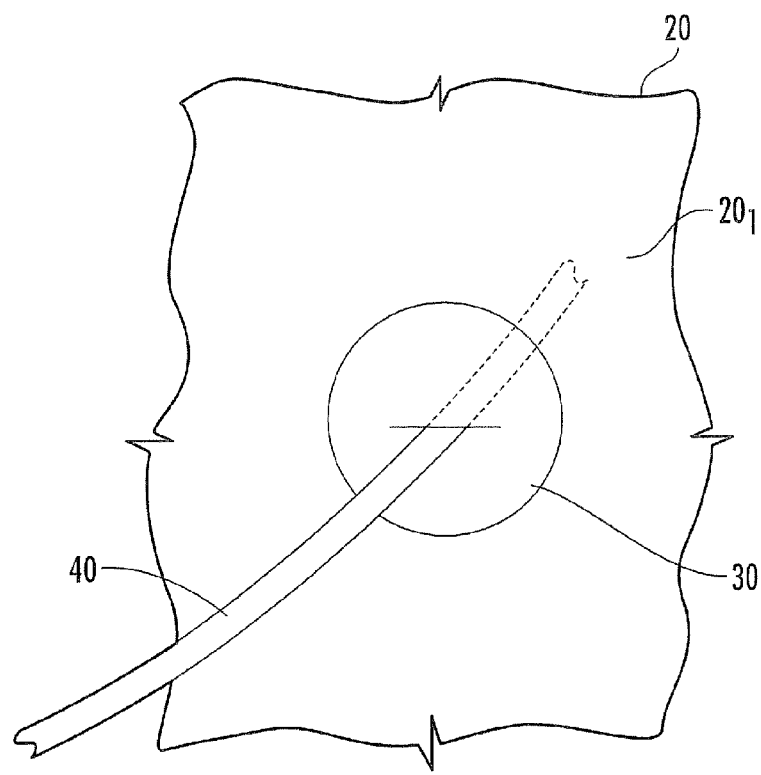
FIG. 2A is a front view of a surgical drape according to some embodiments of the present invention.

FIG. 2A is a front view of the surgical drape 20 illustrated in FIG. 1A. Visible from the front is the first primary surface 20₁ of the surgical drape 20. As shown, the patch 30 is fixably attached to the first primary surface 20₁ of the surgical drape 20. The cable 40 extends snugly through the patch 30. The patch 30 can help support the weight of the cable 40 through the drape 20. The patch 30 can provide a port size that can accommodate a range of cable, tool or instrument sizes. For example, the patch 30 may provide a port size that can accommodate cables, tools or instruments ranging between about ¹⁄₁₆ of an inch to about ¾ of an inch in outer diameter.

The embodiments shown in FIG. 1A, FIG. 1B and FIG. 2A allow for a sterile field on the side of the surgical drape 20 defined by the first primary surface 20₁. The sterile field corresponds to the working region occupied by clinicians. For example, a clinician may introduce a sterile cable, tool or instrument from the sterile side seen as the "near" side of the drape 20 in FIG. 12. The side of the surgical drape 20 defined the second primary surface 20₂ corresponds to the region occupied by a patient. This region is seen as the "opposite" side of the drape 20 in FIG. 12. Because the patch 30 is configured to allow a cable, tool or instrument, such as the cable 40, to extend snugly therethrough, the sterile field can be maintained.

Figure 2B:
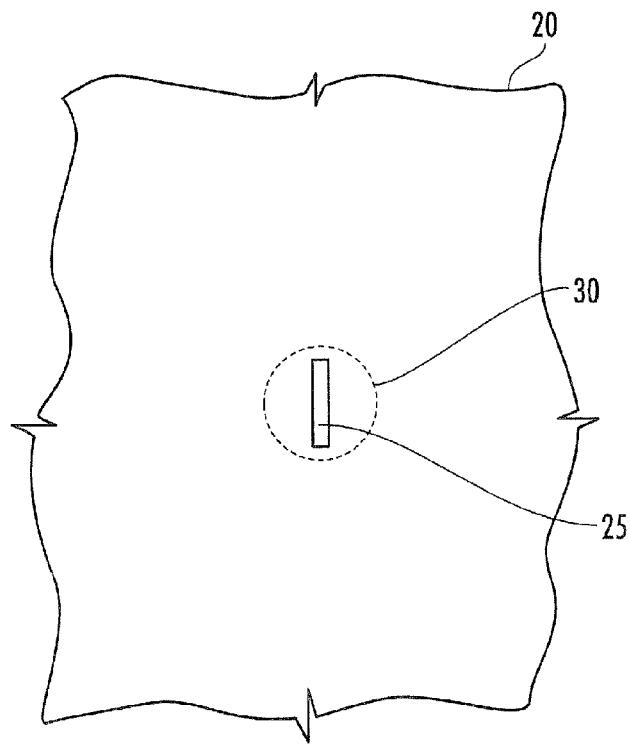
FIG. 2B is a front view of a surgical drape including a preformed perforation(s), aperture or slit according to some embodiments of the present invention.

As exemplified in FIG. 2B, to allow a cable, tool or instrument, such as the cable 40, to extend snugly through the patch, there may be a preformed perforation or a preexisting aperture or slit 25 in the surgical drape 20. In some embodiments, a patch 30 is provided for a clinician to apply to a drape on site prior to surgery. The patch can be applied after the drape is positioned over/on the patient or attached to the magnet housing. The size of the patch 30 is typically larger than the size of the preexisting aperture or slit 25 in the surgical drape 20 (e.g., if the patch 30 is circular, its outer diameter is large enough to cover the entire preexisting aperture or slit 25 in the surgical drape 20, as shown by the dashed lines in FIG. 2B). Because the entire patch 30 covers the preexisting aperture or slit 25, the sterile field is not compromised. Alternatively, as discussed below, a tool and/or the cable or surgical instrument may be used to puncture, cut, or otherwise pierce or open the surgical drape 20 (and/or patch) if there is not a preformed aperture or slit.

Figure 12:
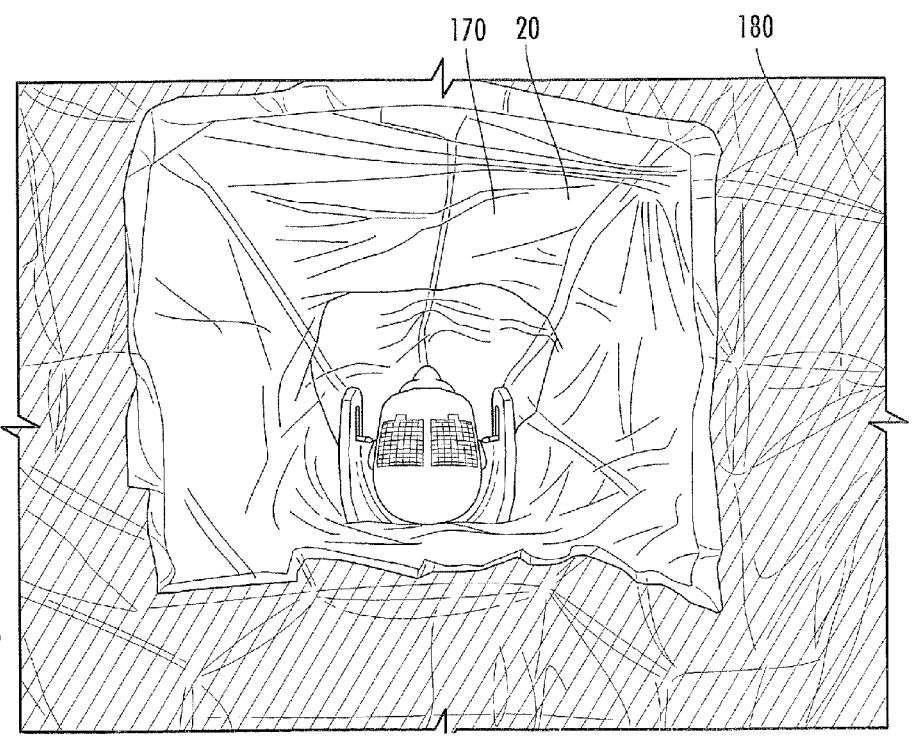
FIG. 12 illustrates the simulated patient and MRI magnet housing shown in FIG. 11 with an attached surgical drape for brain surgeries.

In some embodiments, as shown in FIG. 12, the surgical drape 20 may have a central portion 170 that is visually transmissive and a peripheral portion 180 that may be translucent or opaque (e.g., not visually transmissive). The surgical drape 20 may comprise two or more materials, one of which is visually transmissive and the other may be opaque. The visually transmissive portion 170 of the surgical drape 20 can be constructed of an impervious polymer, such as polyethylene, for example. The visually transmissive portion 170 can allow a clinician to view a patient and/or procedure therethrough. The patch 30 can be fixably attached to a portion of the surgical drape 20 that is visually transmissive. In this regard, the clinician can view a cable, tool or instrument as it is being extended through the patch 30 and surgical drape 20.

Figure 3A:
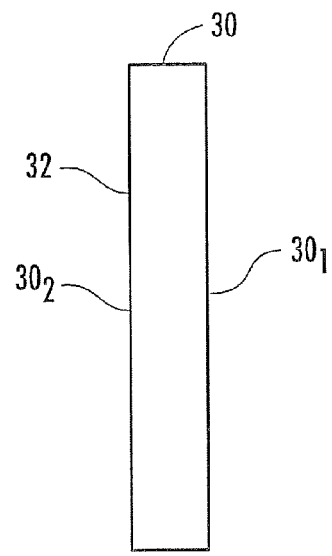
FIG. 3A is an enlarged side view of a patch according to some embodiments of the present invention.

FIG. 3A is a side view of a patch 30 according to some embodiments of the present invention. The patch 30 has opposing first and second primary surfaces 30₁, 30₂. In the embodiment shown in FIG. 3A, the second primary surface 30₂ can include an adhesive layer 32. The adhesive layer 32 may cover the entire second primary surface 30₂ or only a predetermined portion such as a peripheral portion of the second primary surface 30₂ as indicated by the shaded region in FIG. 3B. In some embodiments, and as shown in FIG. 3A, only one of the opposing first and second primary surfaces 30₁, 30₂ includes an adhesive layer 32. In this regard, the patch with one opposing surface including the adhesive layer 32 is configured to be fixably attached to a surgical drape 20 via the adhesive layer 32.

Figure 3B:
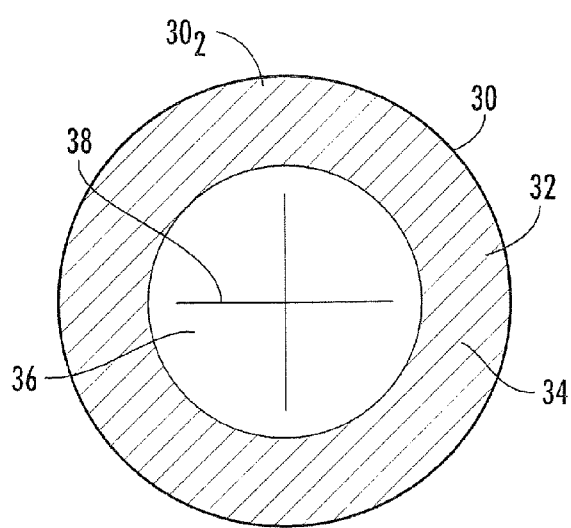
FIG. 3B is a rear view of a patch according to some embodiments of the present invention.

FIG. 3B is a rear view of the patch 30 according to some embodiments of the present invention. Visible from the rear is the second primary surface 30₂ of the patch 30. The patch 30 includes a peripheral portion 34 and a central portion 36. In some embodiments, and as shown in FIG. 3B, only the peripheral portion 34 of the patch 30 includes an adhesive layer 32. The adhesive layer 32 allows the second primary surface 30₂ of the patch 30 to be fixably attached to a surgical drape 20. Alternatively, the entire second primary surface 30₂ of the patch 30 may include an adhesive layer 32.

Figure 3C:
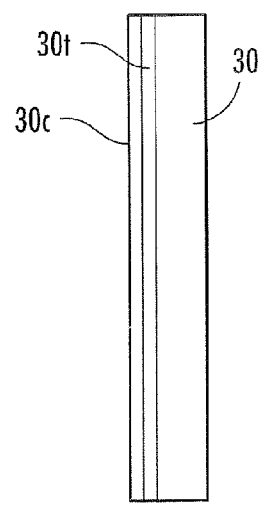
FIG. 3C is an enlarged side view of a patch according to some embodiments of the present invention.

In some embodiments, such as when the patch 30 is supplied separately from the surgical drape 20 (e.g., in a kit allowing a clinician to select the location of the patch 30 on the surgical drape 20, as described below), the adhesive layer 32 can be provided with an overlying cover, such as a peel-away cover 30c or the equivalent (FIG. 3C). Where only the peripheral portion 34 of the patch 30 includes the adhesive layer 32, the cover 30c may be shaped to cover only the peripheral portion. The cover 30c prevents the adhesive layer 32 from inadvertently sticking to unintended objects and/or picking up contaminants. In some embodiments, the adhesive layer 32 can be provided by double-sided sticky tape 30t.

Figure 3D:
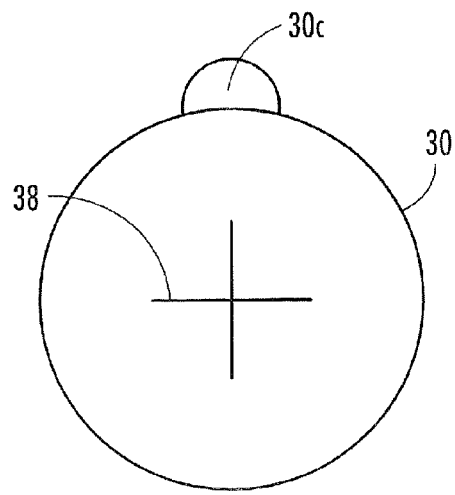
FIG. 3D is a front view of a patch according to some embodiments of the present invention.

Referring to FIG. 3D, in some embodiments, the cover 30c can include a tab that extends past the outer periphery of the patch 30. The tab may be useful in removing the cover 30c so as to expose the adhesive layer 32 of the patch 30.

According to still other embodiments, neither the first primary surface $30_1$ nor the second primary surface $30_2$ of the patch 30 includes an adhesive layer. In such embodiments, a clinician may fixably attach one of the opposing primary surfaces $30_1$, $30_2$ of the patch 30 to a surgical drape in situ with adhesive or double-sided tape provided as a separate component, for example.

Returning to FIG. 3B, at least the central portion 36 of the patch 30 may be preferentially scored and/or include a thinner region to create a slit 38. The slit 38 can extend through the entire thickness of the patch 30; that is, the slit 38 may be visible on both opposing first and second primary surfaces $30_1$, $30_2$. Alternatively, the slit 38 may partially extend through the entire thickness of the patch 30 so that one primary surface is intact prior to use. The slit 38 allows for a cable, tool or instrument to pass through the patch 30 while still being snugly held in place (i.e., clamped) by the patch 30. The slit 38 may also be configured to allow cables, tools or instruments of different sizes and/or multiple cables, tools and/or instruments to pass through and be snugly held by the patch 30.

In some alternative embodiments, the patch 30 does not include perforations or a slit. Rather, the patch 30 can be configured to be punctured by a sterile hand-held tool such as a protective cap attached to a cable or surgical instrument that can be extended through and snugly held by the patch. Such tools and/or caps may be provided as separate components of a surgical system or included in a kit as discussed in more detail below.

Figure 3E:
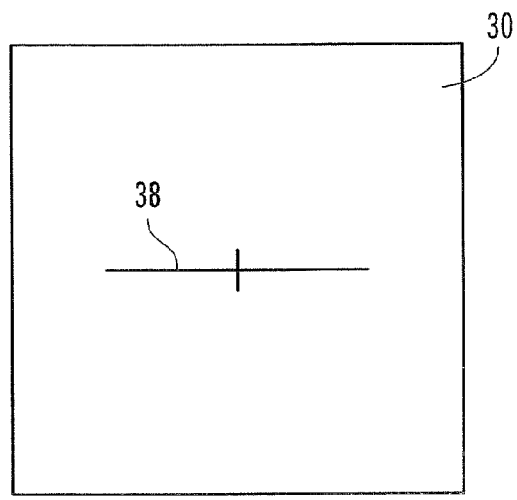
FIG. 3E is a front view of a patch according to an alternative embodiment of the present invention.

It is noted that the patch 30 in the embodiments shown in FIG. 3B and FIG. 3D is shown as circular and as shown in FIG. 3E is square or rectangular. The patch 30 can have a top surface area of between about 1.75 square inches (11.3 square centimeters) to about 10 square inches (65 square centimeters). The central portion 36 of the patch 30 can have a top surface area of between about 0.2 square inches (1.3 square centimeters) to about 3.2 square inches (21 square centimeters). Each preferential score of the slit 38 can have a length of between about 0.4 inches (1 centimeter) to about 1.9 inches (4.8 centimeters). The patch 30 can have a thickness of between about 0.05 inches (0.1 centimeters) to about 0.5 inches (1.3 centimeters). Although the patch 30 is shown as circular in FIG. 3B and FIG. 3D and square or rectangular in FIG. 3E, other shapes such as triangles, hexagons and other polygons or geometries may be used including irregular geometries. Additionally, although the slit 38 has an "X" and/or cross-hair shape in FIG. 3B and FIG. 3D, other configurations are contemplated, such as a single scored line, a star shape, an "S" and/or curved shape, or combinations thereof.

In some embodiments, the patch 30 may comprise a polymer, copolymer or derivative thereof, such as silicone, for example. In some embodiments, the patch 30 includes an inner portion, such as the central portion 36 seen in FIG. 3B, with a relatively flexible material and an outer portion, such as the peripheral portion 34 seen in FIG. 3B, that has increased structural rigidity relative to the inner portion. For example, the inner portion may be thinner than the outer portion and/or the inner portion may comprise a different, more flexible material than the outer portion. The patch 30 can be planar and flexible to conform to underlying material. In some embodiments, the patch 30 has increased structural rigidity relative to the portion of the surgical drape it is affixed to. For example, a patch 30 of silicone can have increased structural rigidity relative to a polyethylene portion of a drape 20. In any event, in some embodiments, both the drape 20 and the at least one patch 30 can be constructed of MRI-compatible materials such that they are suitable for use in MRI surgical procedures.

Figure 4:
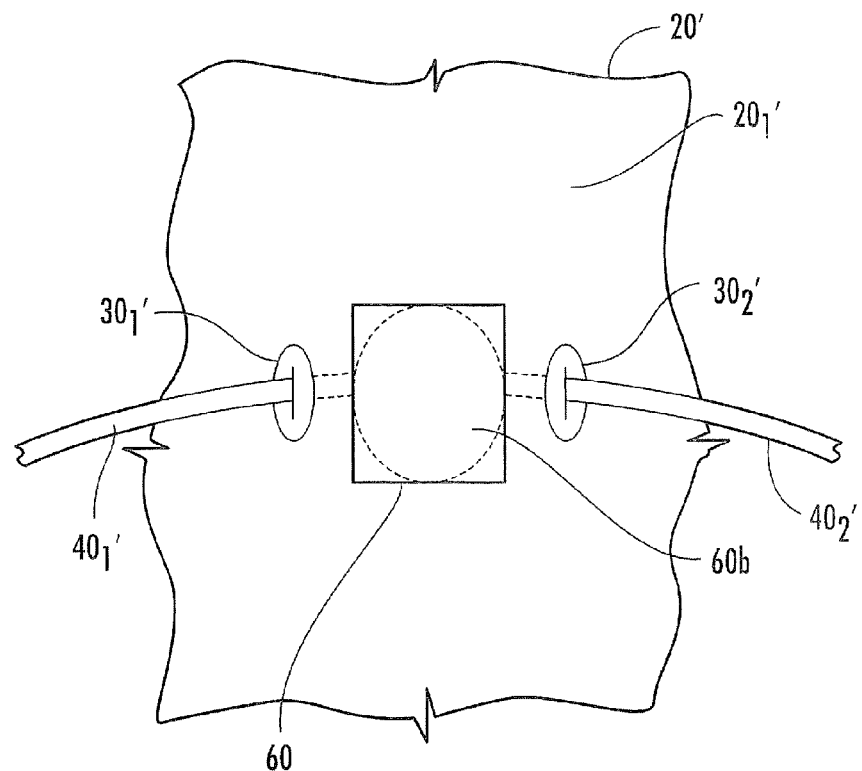
FIG. 4 is a schematic illustration of a surgical drape with cable-port patches for use in bilateral MRI procedures according to some embodiments of the present invention.

FIG. 4 illustrates a flexible surgical drape 20' for use in bilateral MRI procedures. According to this embodiment, a surgical drape 20' has opposing first and second primary surfaces $20_1$' and $20_2$'. Only the first primary surface $20_1$' is labeled in the view presented in FIG. 4. An MRI magnet housing 60 defining a bore 60b for MRI procedures is located on one side of the surgical drape 20' defined by the second primary surface $20_2$'. As shown, first and second patches $30_1$', $30_2$' are fixably attached to the surgical drape 20' on the side defined by the first primary surface $20_1$'. The two patches $30_1$', $30_2$' are positioned such that cables, tools or instruments, such as cables $40_1$', $40_2$', routed therethrough can approach opposite sides of the MRI magnet housing 60. A first cable $40_1$' extends through and is snugly held by the first patch $30_1$' and a second cable $40_2$' extends through and is snugly held by the second patch $30_2$'. An end of each of the first and second cables $40_1$', $40_2$' may include connectors (not pictured), such as BNC connectors.

The embodiment shown in FIG. 4 allows for a sterile field on the side of the surgical drape 20' defined by the first primary surface $20_1$'. The sterile field corresponds to the working region occupied by one or more clinicians. The side of the surgical drape 20' defined the second primary surface $20_2$' corresponds to the region occupied by a patient. Because the patches $30_1$', $30_2$' are configured to allow cables, tools or instruments, such as the cables $40_1$', $40_2$', to extend snugly therethrough, the sterile field can be substantially maintained and/or not compromised.

Figure 5:
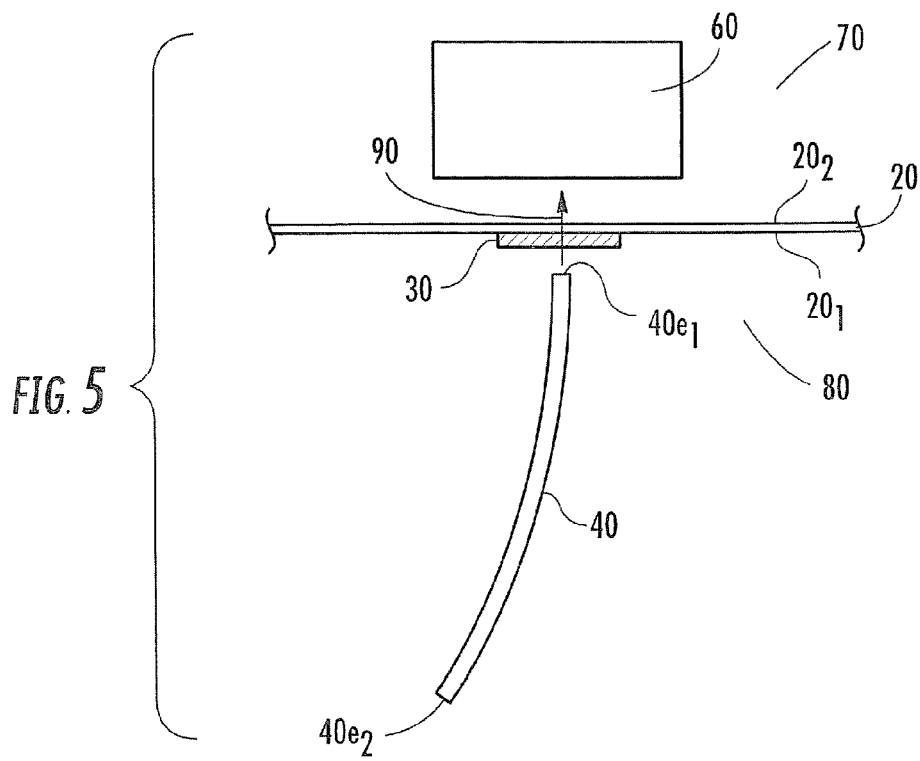
FIG. 5 is a schematic illustration of a cable that can be slidably advanced through a cable-port patch into a surgical environment according to some embodiments of the present invention.

FIG. 5 illustrates a method for introducing a cable, tool, or instrument into a surgical environment while maintaining a sterile field. In the illustrated embodiment, a surgical drape 20 is provided having first and second opposing primary surfaces $20_1$, $20_2$, wherein the first primary surface $20_1$ defines a sterile side 80 and the second primary surface $20_2$ defines a non-sterile side 70 (or at least a side that has an increased risk and/or is subject to exposure to a non-sterile environment or conditions during a surgical procedure). At least one patch 30 is fixably attached to the first primary surface $20_1$ defining the sterile side 80. As indicated by arrow 90, a first end portion $40e_1$ of a sterile cable 40 is introduced through the patch 30 and the sterile drape 20 into the non-sterile side 70 of the surgical drape 20, with the patch 30 snugly holding (i.e., clamping) the cable 40. In this regard, the portion of the cable 40 that is not introduced through the patch 30, including a second end portion $40e_2$, maintains its sterility on the sterile side 80. In some embodiments, a surgical suite is provided with an MRI magnet housing 60 defining a bore 60b (see FIGS. 5 and 11) for MRI procedures, with the MRI magnet housing 60 residing on the non-sterile side 70 of the surgical drape 20.

In some embodiments, the patch 30 is fixably attached to the first primary surface $20_1$ of the drape 20 defining the sterile side 80 of the drape 20 before the drape 20 is provided. In order to introduce the cable 40 through the patch 30, the patch 30 may be preferentially scored, as described above. Alternatively, the patch 30 and/or the surgical drape 20 may be punctured in situ by a clinician with a tool or a protective cap attached to the end of the cable 40, as described in more detail below. Likewise, in order to introduce at least a portion of the cable 40 through the surgical drape 20 and into the other side, the surgical drape 20 may optionally have a preexisting hole, slit or perforation that is smaller in size than the overlying patch 30.

Figure 8A:
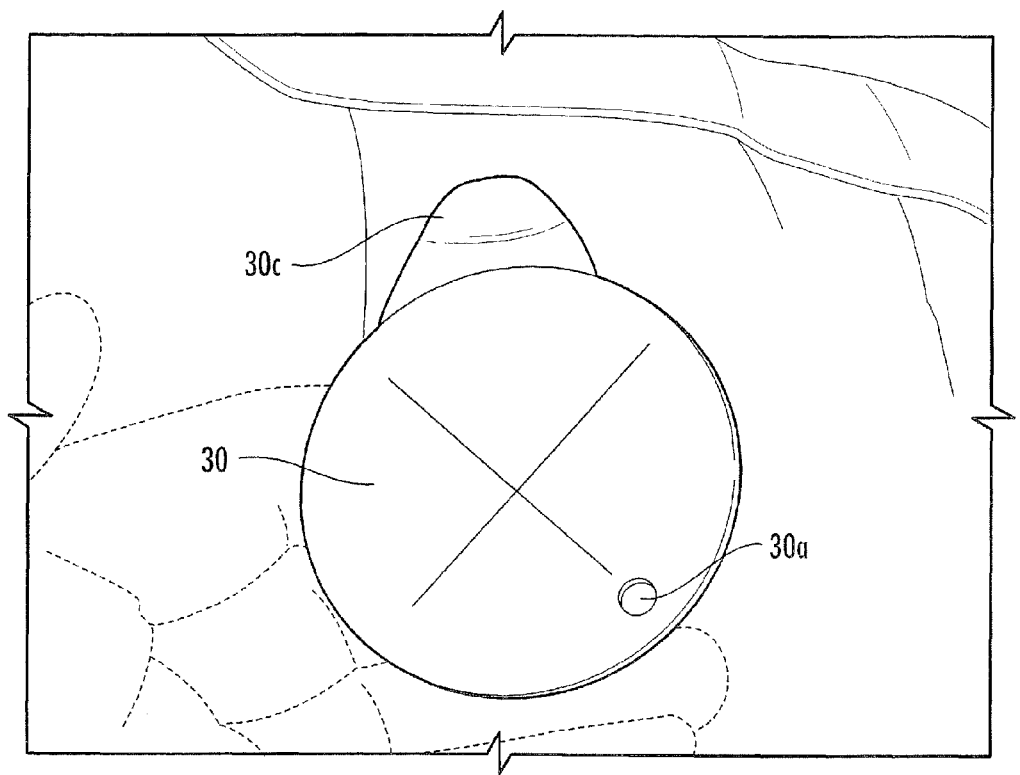
FIGS. 8A through 8O illustrate a method and components useful for introducing a cable through a surgical drape into a surgical environment according to some embodiments of the present invention.
Figure 8B:
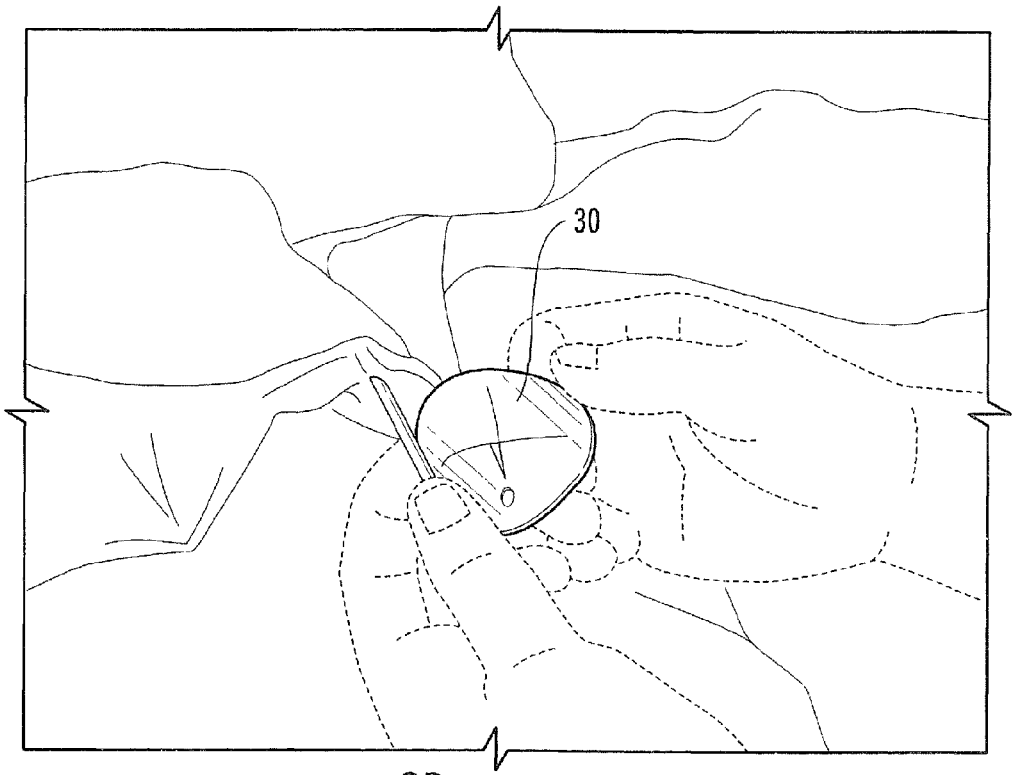
Figure 8C:
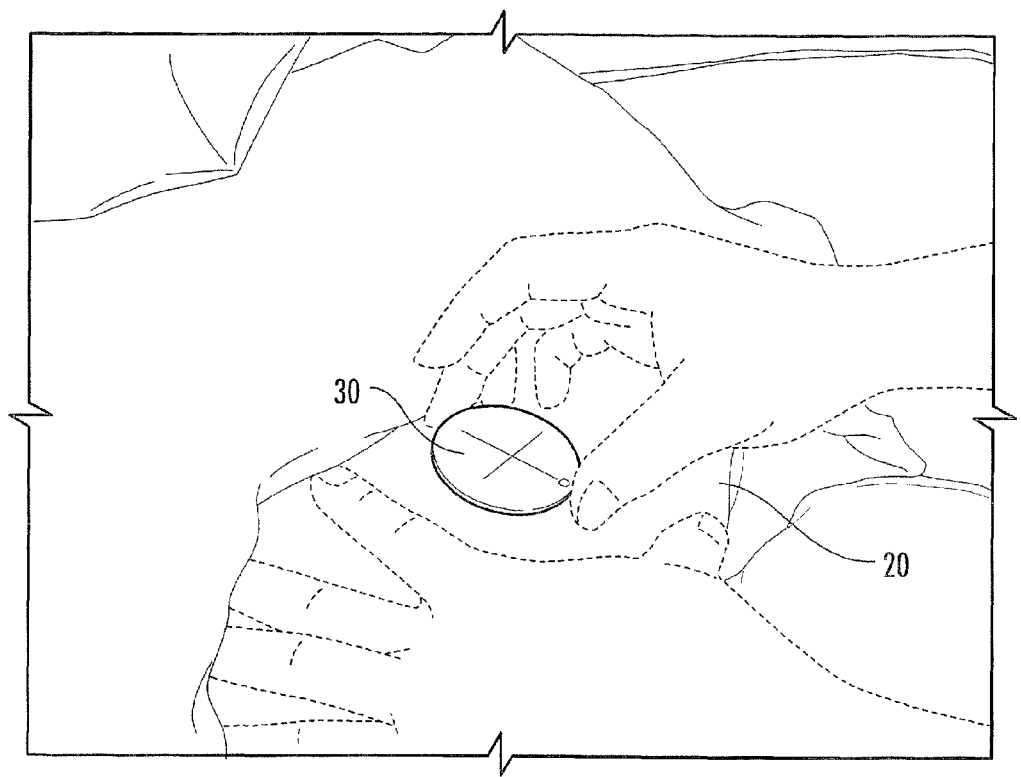
Figure 8D:
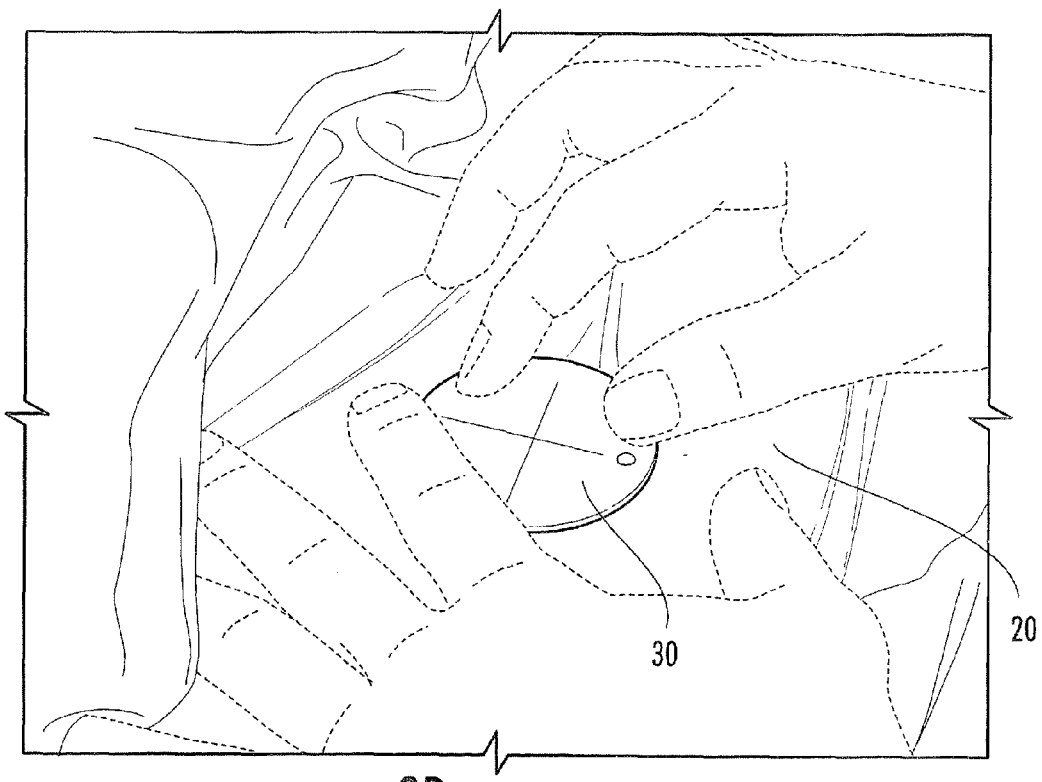
Figure 8E:
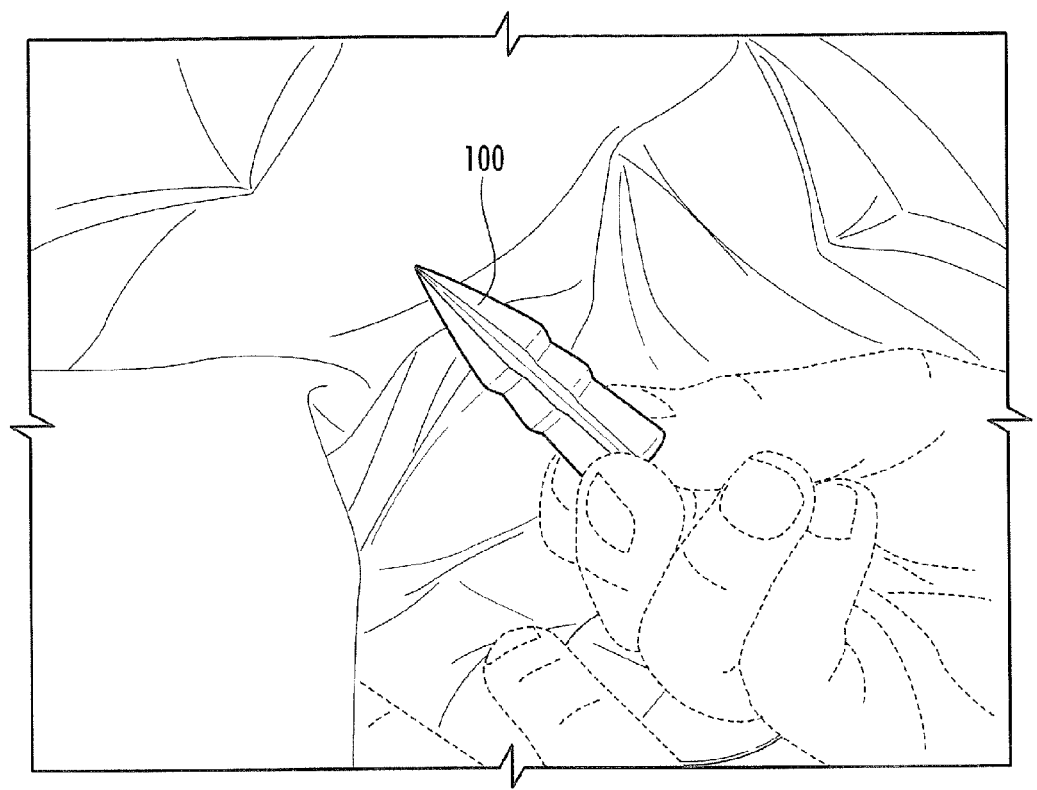
Figure 8F:
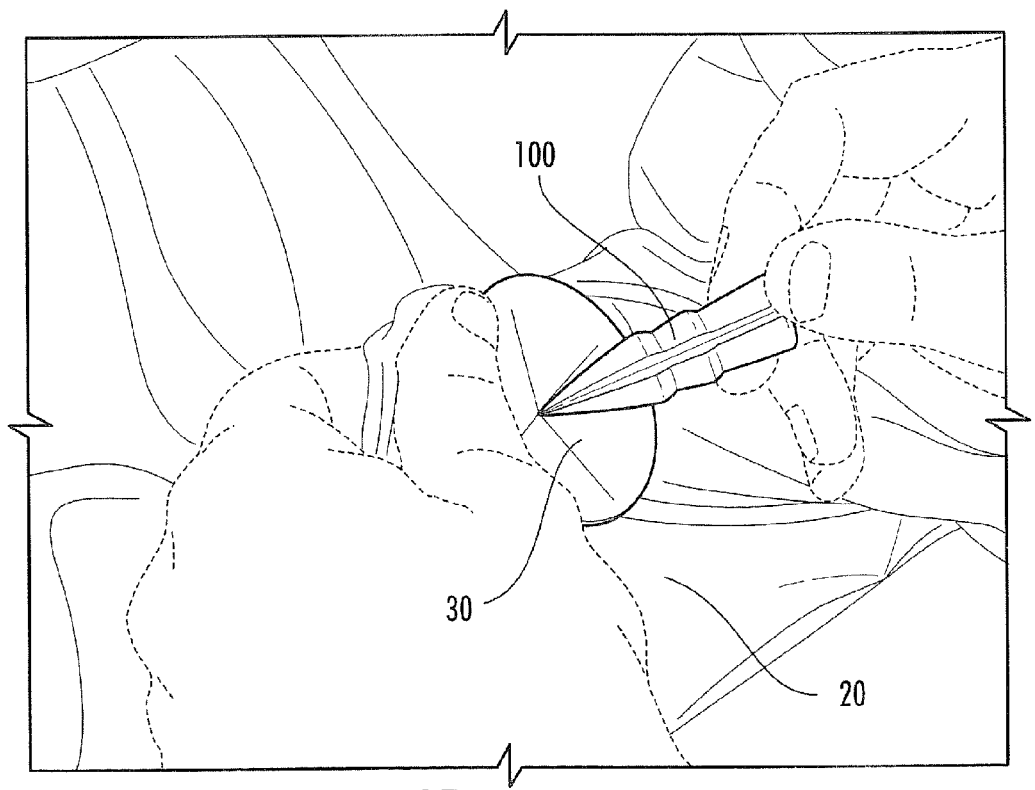
Figure 8G:
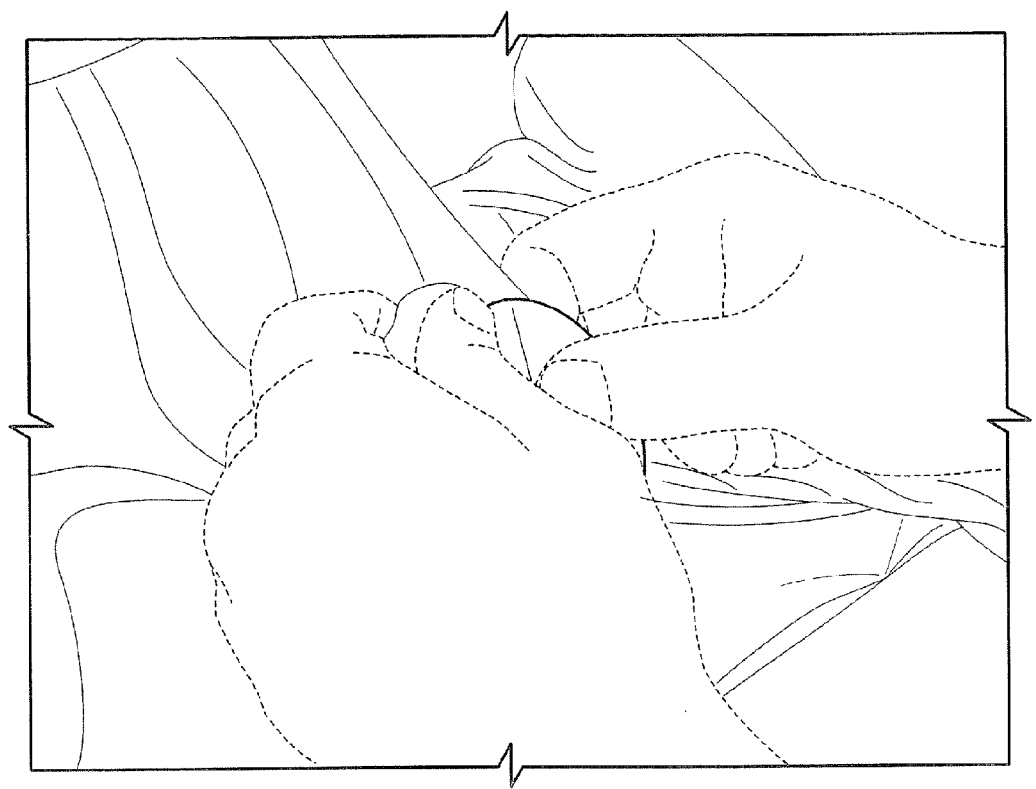
Figure 8H:
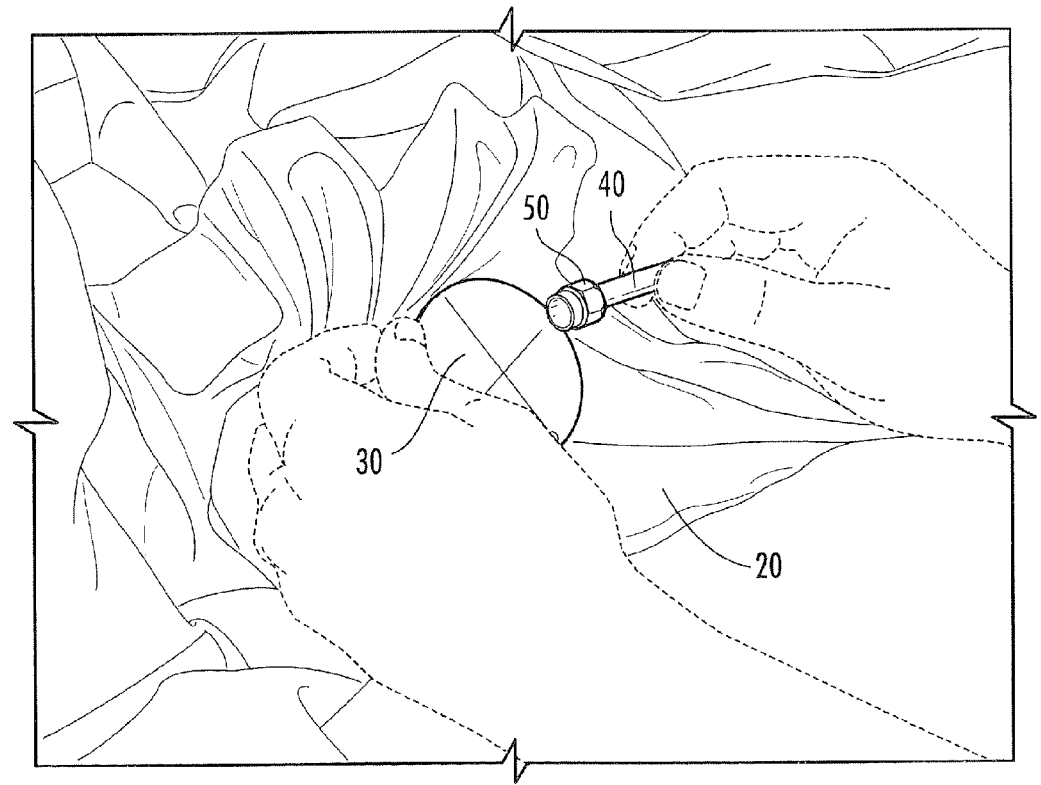
Figure 8I:
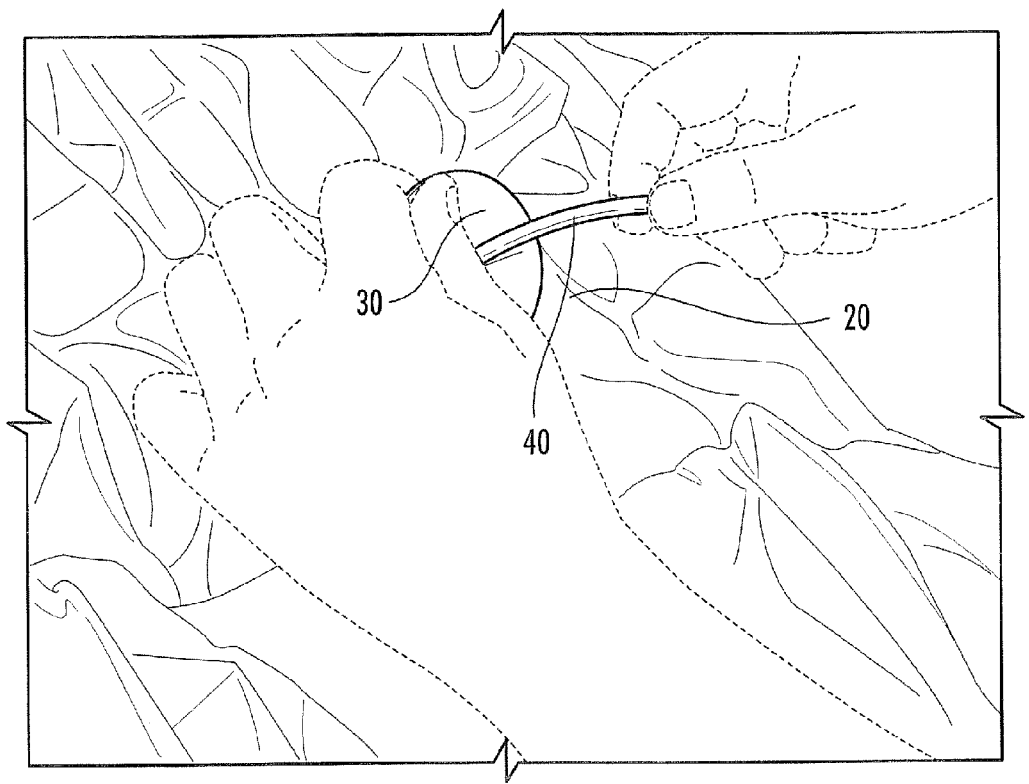
Figure 8J:
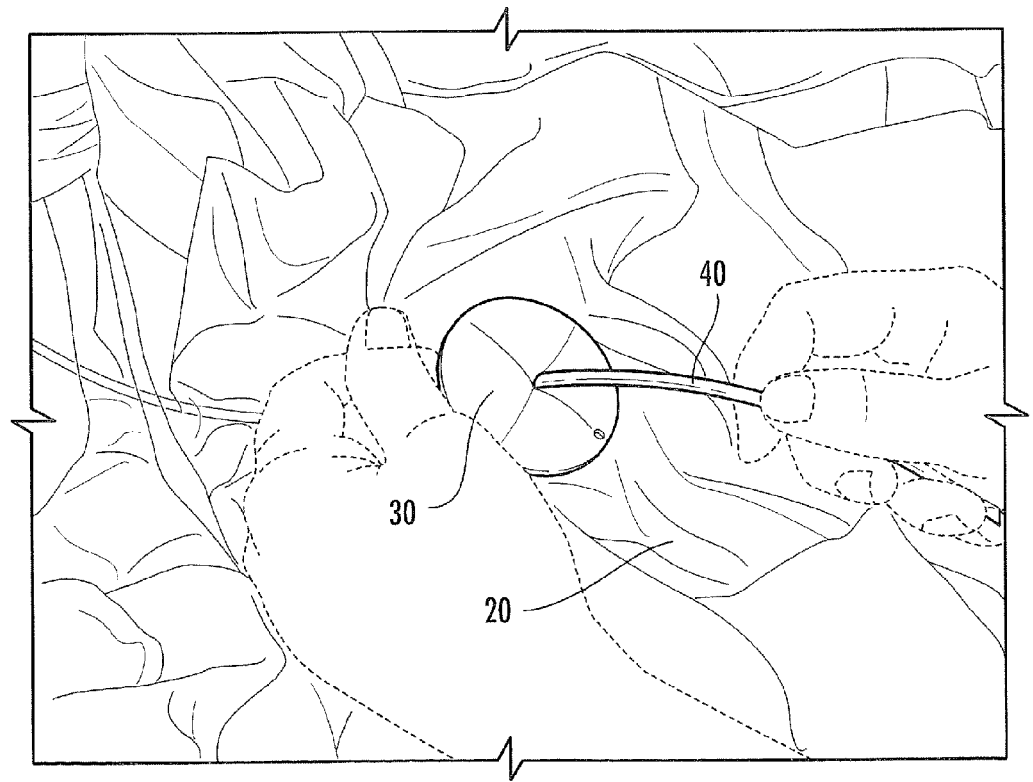
Figure 8K:
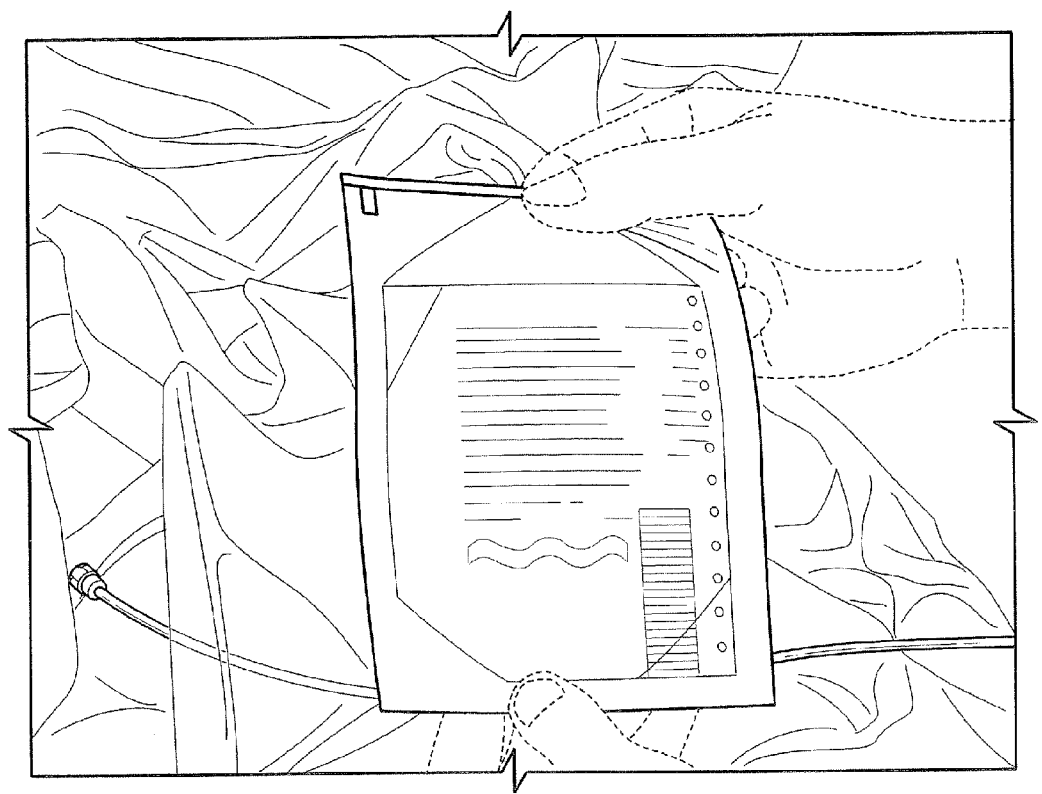
Figure 8L:
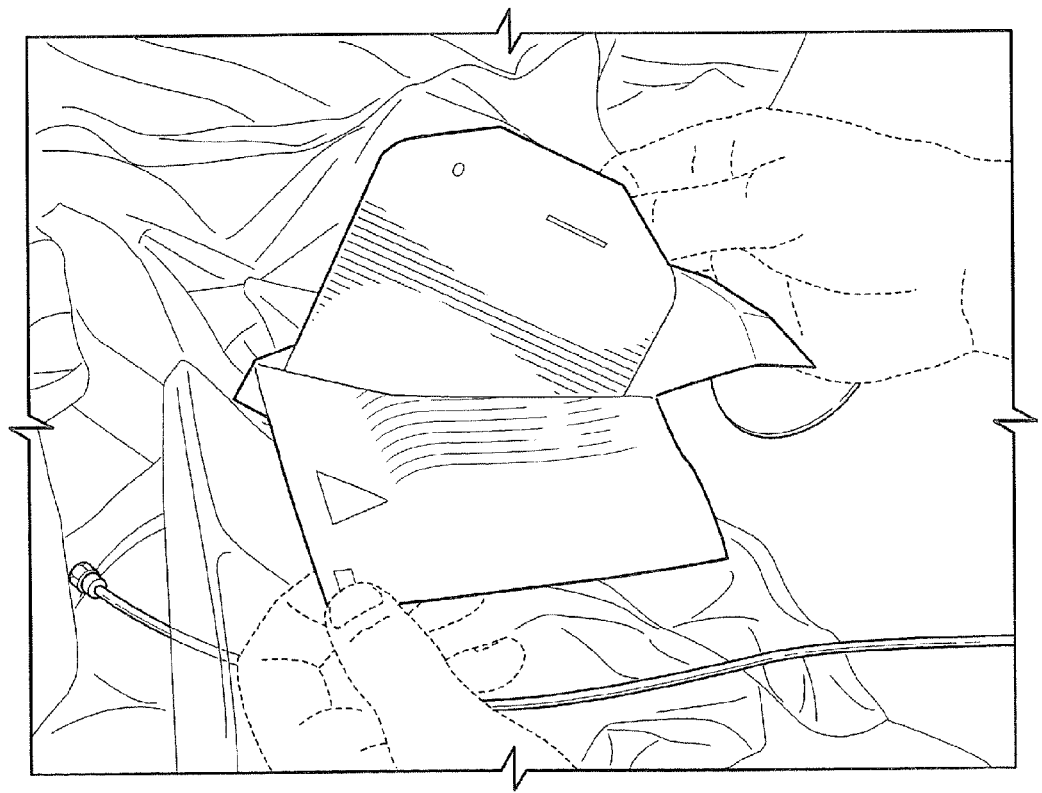
Figure 8M:
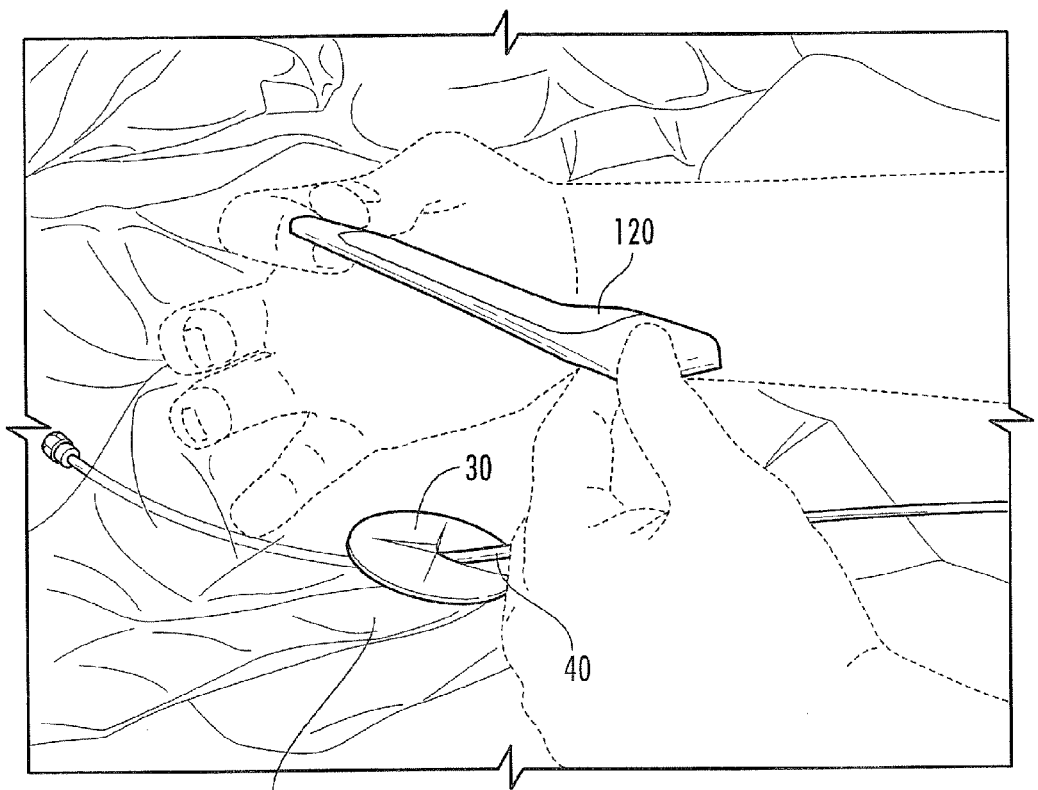
Figure 8N:
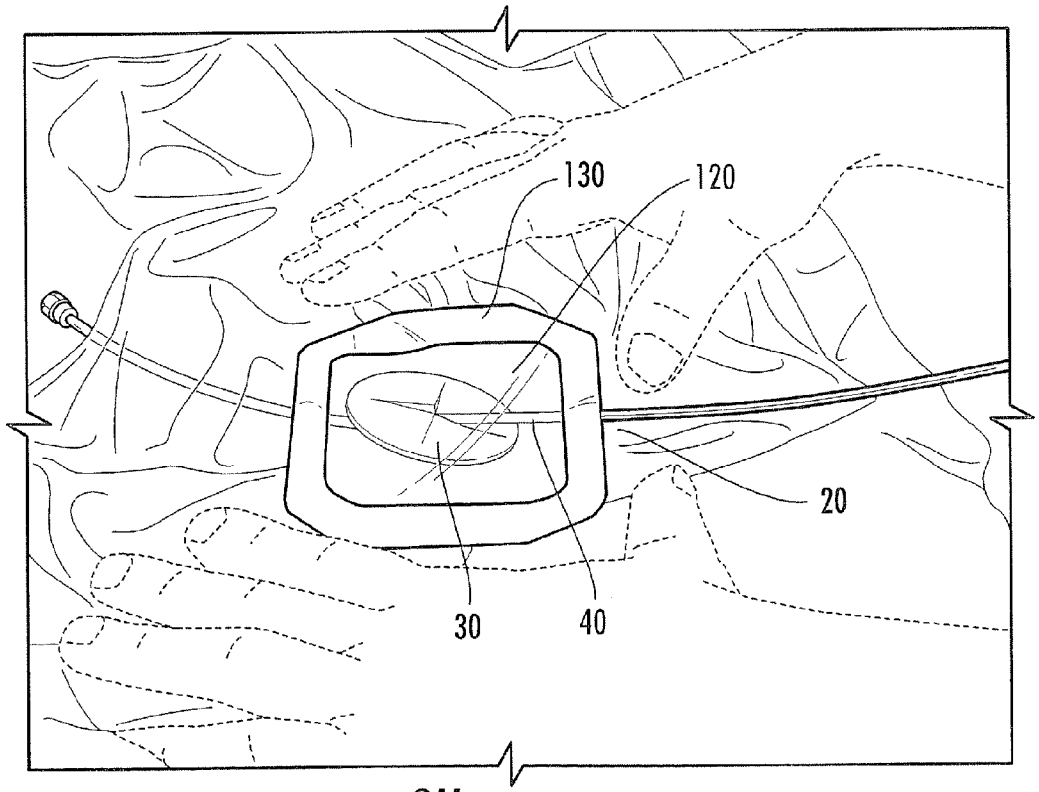
Figure 8O:
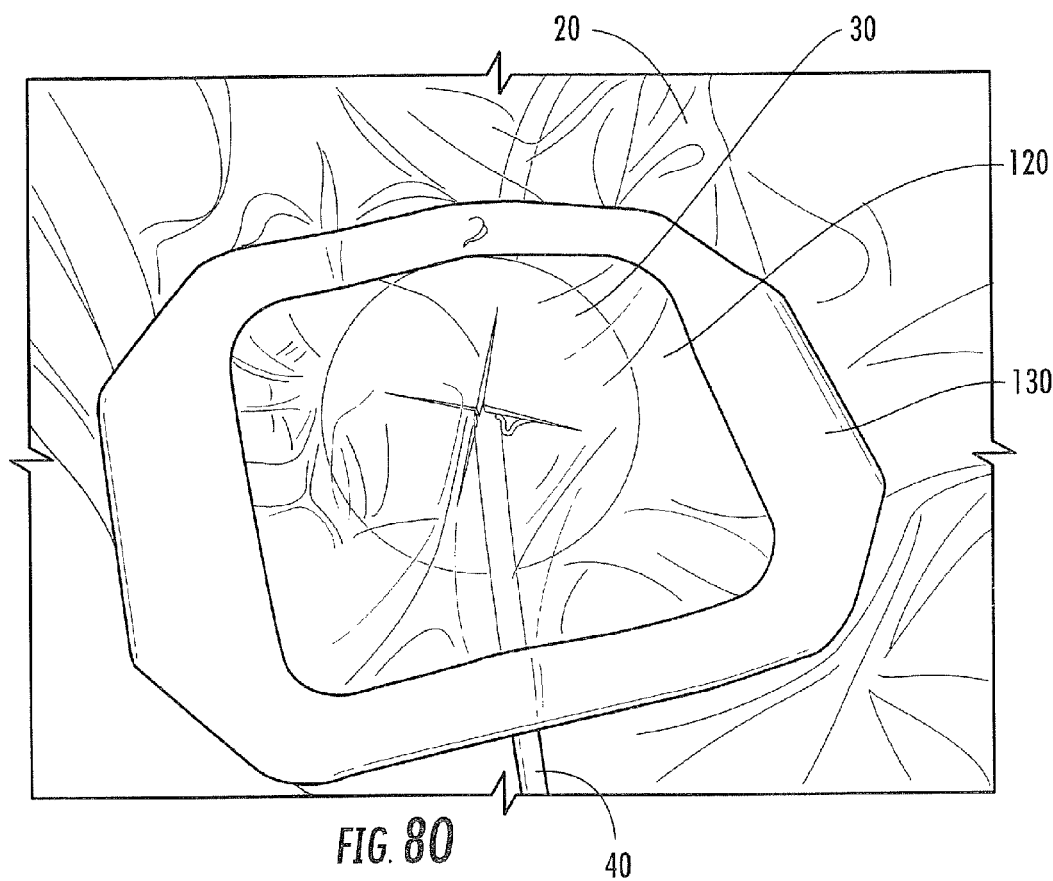

FIGS. 8A through 8O illustrate an exemplary series of steps and associated components for introducing a cable, tool or instrument into a surgical environment while maintaining a substantially sterile field. As shown in FIGS. 8A through 8D, a patch 30 is provided. The patch 30 may have an adhesive layer. The patch 30 may further have a releasable cover 30c overlying the adhesive layer, as shown in FIG. 8A. At this point, the patch 30 may be fixably attached to a surgical drape 20, as shown in FIGS. 8C and 8D. In the embodiment shown in FIG. 8A, the patch 30 includes a aperture or hole 30a, which may facilitate alignment of the patch 30 on the surgical drape 20, for example.

As shown in FIGS. 8E through 8G, a sterile tool 100 may be provided to puncture, slice or pierce the patch 30 and/or the surgical drape 20. The tool 100 is described in more detail below. The tool 100 can be single-use disposable.

With the patch 30 and/or the surgical drape 20 now punctured, sliced or pierced, a cable, tool or other instrument, such as the cable 40 shown in FIGS. 8H through 8J, may be extended through the opening in the patch 30 and surgical drape 20. As seen in FIG. 8H, the cable may include a connector 50, such as a BNC connector, for example. The patch 30 may serve to snugly hold (i.e., clamp) the cable 40. Because the patch 30 is configured to allow cables, tools or instruments, such as the cable 40 to extend snugly therethrough, the sterile field can be substantially maintained and/or not compromised.

As shown in FIGS. 8K through 8O, a coverlay 120 can be placed over the patch 30 and the cable 40 extending therethrough. The coverlay 120 may serve the purpose of further substantially maintaining the sterile field. Additionally or alternatively, the coverlay 120 may serve the purpose of preventing the cable 40 from shifting, sliding or otherwise moving after it has been extended through the patch 30 and situated as desired. The coverlay 120 can be a film such as a wound dressing such as Tegaderm™ available from 3M. The coverlay 120 may be sterile, and may be a wound dressing, including a commercially available wound dressing. The coverlay 120 may be visually transmissive, such as to allow a clinician to view the patch 30 and the cable 40 through the coverlay 120. The coverlay 120 may include a periphery 130 that includes an adhesive layer to affix the coverlay 120 to the surgical drape 20, such that the coverlay may be positioned over the patch 30 and cable 40, as shown in FIGS. 8N and 8O. There may be a releasable outer cover overlying the adhesive layer of the coverlay 120.

Figure 9A:
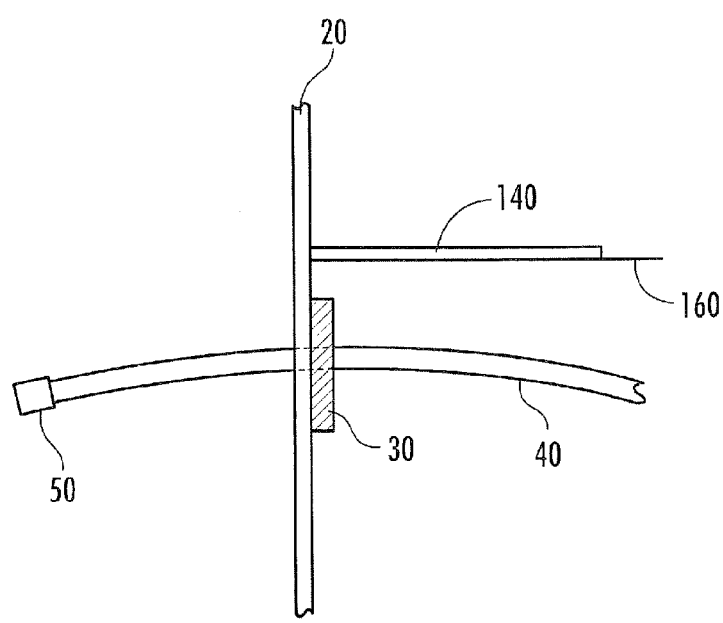
FIG. 9A is a side view of a surgical drape with a port-patch according to some embodiments of the present invention.
Figure 9B:
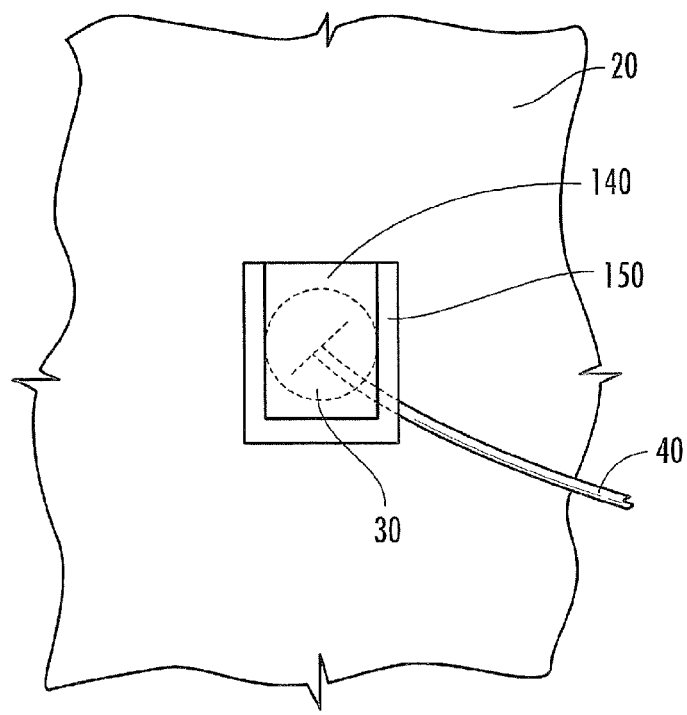
FIG. 9B is a front view of the patch and surgical drape shown in FIG. 9A.

As shown in FIGS. 9A and 9B, in some embodiments it is contemplated that the surgical drape 20 or the patch 30 may include a fold-over flap 140 that forms the coverlay 120 which may serve the purpose of further substantially maintaining the sterile field and/or preventing the cable 40 from shifting, sliding or otherwise moving after it has been extended through the patch. The flap 140 is extended outward for ease of reference in the side view of FIG. 9A, but it is generally contemplated that the flap 140 can lay flat against the surgical drape 20 prior to manipulation by a clinician. Although the surgical drape 20 includes the flap 140 in FIG. 9A, it is also contemplated that the patch 30 includes the flap 140. The flap 140 may include a periphery 150, at least a portion of which may include an adhesive layer. There may be a releasable cover 160 overlying the adhesive layer. Once the patch 30 has been situated on the surgical drape 20 and the cable 40 has been extended therethrough, as described above, the flap 140 may be positioned over the patch 30 and the cable 40, as shown in FIG. 9B. The flap 140 may be visually transmissive, such as to allow a clinician to view the patch 30 and the cable 40 through the flap 140.

Figure 10A:
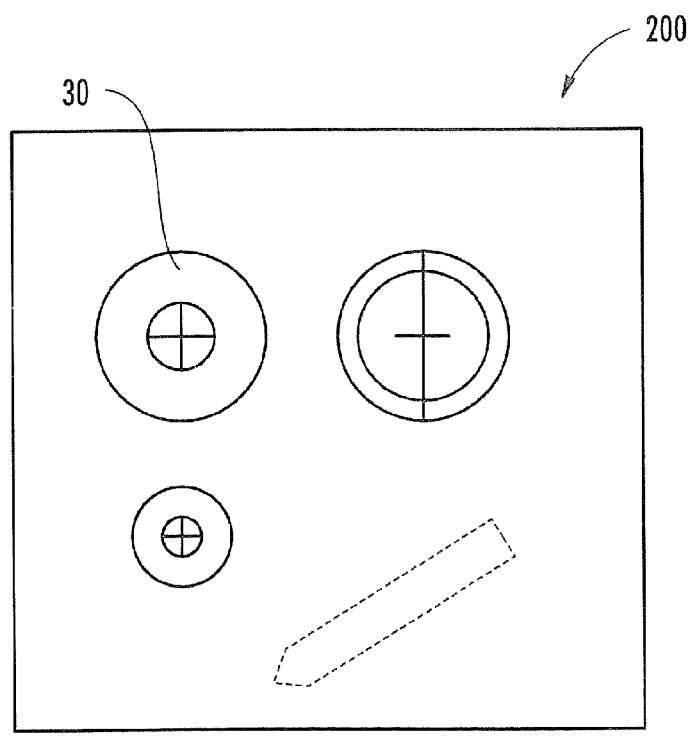
FIG. 10A is a schematic illustration of a kit including cable-port patches according to some embodiments of the present invention.

FIG. 10A illustrates an example of a medical kit 200. As shown, the medical kit 200 includes at least one patch 30, and typically a plurality of patches of the same or different sizes which can provide the same or different port sizes. The patches may be separately packaged or packaged together as a bundle in sterile packaging. One side of the patches may have an adhesive layer which is covered with a peel-away cover as described above. This configuration may be desirable for some procedures or for some surgeons as it allows a clinician to arrange the surgical drape 20 and select the position of the patch 30 as desired for a particular procedure in situ. The kit 200 can optionally include the surgical drape 20 (not shown). The optional surgical drape 20 may include a fold-over flap 140 or the at least one patch 30 may include the fold-over flap 140, as described above. Alternatively, the kit can optionally include a coverlay 120, as described above.

Figure 6:
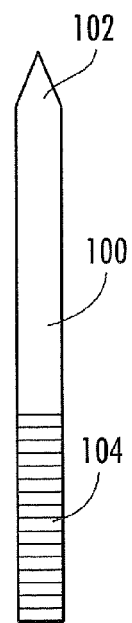
FIG. 6 is a front view of a tool suitable for introducing an aperture into a cable-port patch according to some embodiments of the present invention.

The medical kit 200 may further optionally include a hand-held tool 100 (FIG. 6) including a tip 102 which is designed to puncture, slice or pierce the patch 30 and/or the surgical drape 20. The tool 100 may also include a hand grip 104. The tool 100 can be further designed to form a passage in the patch 30 that is only large enough to allow a cable or instrument to pass through while snugly holding (i.e., clamping) the cable or instrument. In this regard, a sterile side of the surgical drape 20 is not compromised. In other embodiments, the medical kit 200 may include a plurality of tools 100 for use with differently sized cables and/or instruments.

Figure 7:
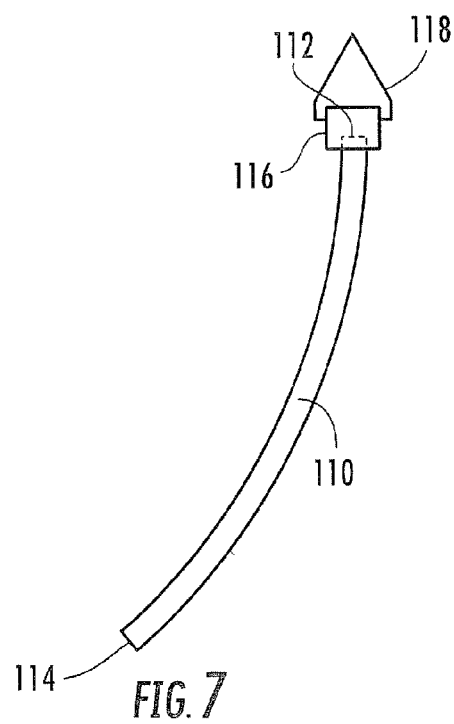
FIG. 7 is a front view of a cable including a removable cap for introducing a cable through a surgical drape into a surgical environment according to some embodiments of the present invention.

Alternatively, the kit may include an instrument, such as a cable 110 with opposing first and second ends 112, 114 and a cap 118 as shown in FIG. 7. A connector 116, such as a BNC connector, may be provided at the first end 112 of the cable 110 and the cap 118 can be placed over the connector 116. The cap 118 can have a configuration that defines a puncture tool, a piercer or other opening mechanism. The cap 118 can manually puncture the patch 30 and/or the surgical drape 20. The cap 118 can form a passage in the patch 30 that allows the cable 110 to pass through while snugly holding (i.e., clamping) the cable 110 (and maintaining a sterile side of the surgical drape 20, where the second end 114 of the cable 110 resides). It is noted that the medical kit may include a sterile cap, as opposed to a cap already attached to a cable, tool or instrument. The cap may be sized to fit over standard connectors, such as BNC connectors, for example.

Figure 10B:
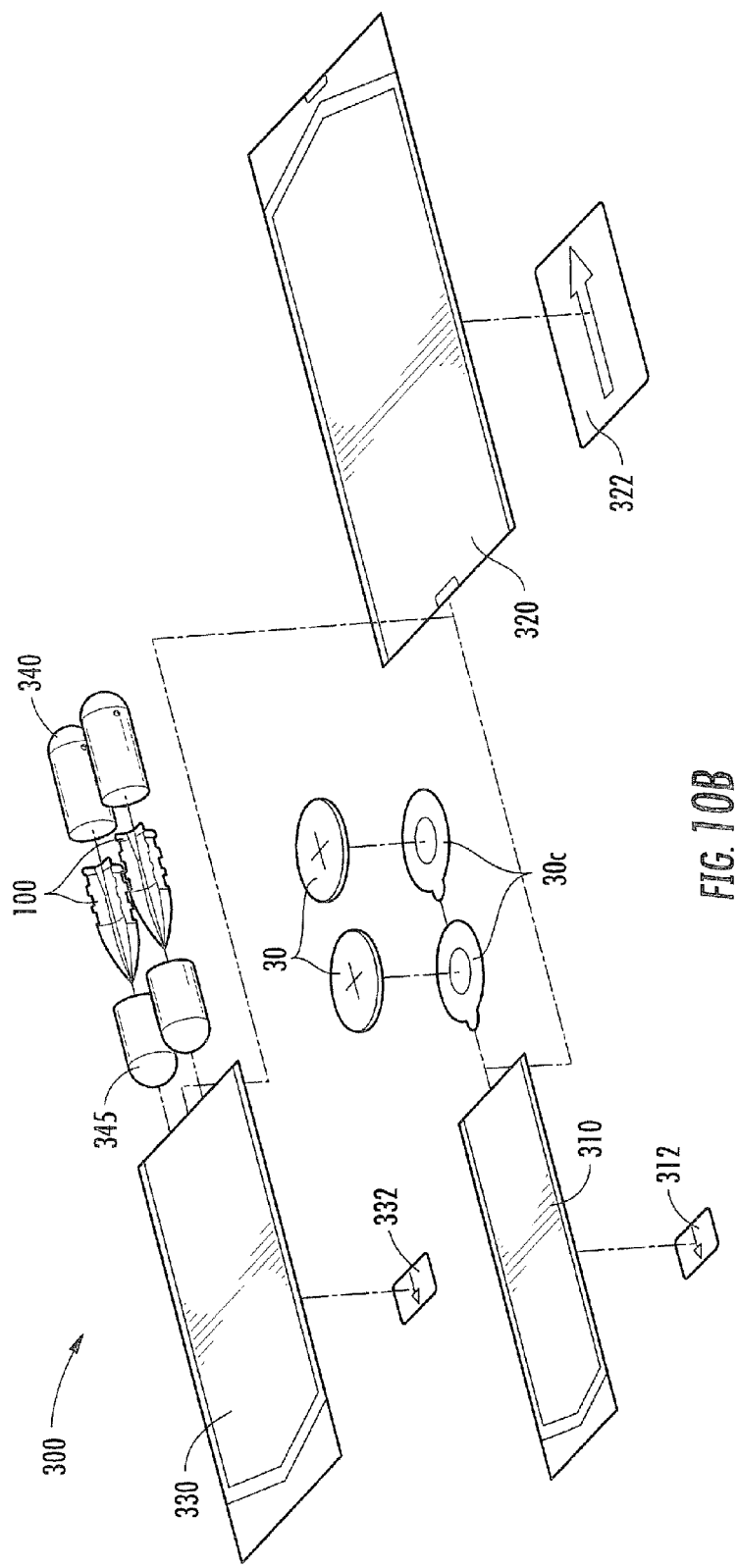
FIG. 10B is an exploded view of a kit including cable-port patches and tools according to some embodiments of the present invention.

A medical kit 300 is illustrated at FIG. 10B. The kit typically includes at least one patch 30. Each patch 30 may include an adhesive layer and a peel-away cover 30c, as described in more detail above. A plurality of patches 30 may be packaged together in sterile packaging such as a pouch 310, which may be sealed closed to allow the patches 30 to maintain their sterility. The pouch 310 is preferably made of a strong material that is difficult to tear, but can be cut open when the patches 30 are to be used. An exemplary material is Tyvek® available from DuPont. A label 312 may be affixed to or printed on the patch 310. The label 312 may include information such as a lot number and expiration date, for example.

The kit 300 may include at least one tool 100 for puncturing, slicing, or piercing the patches 30 and/or a surgical drape, as described in more detail above. A plurality of tools 100 may be packaged together in sterile packaging such as a pouch 330, which may be sealed closed to allow the tools 100 to maintain their sterility. The pouch 330 is preferably made of a strong material that is difficult to tear, but can be cut open when the tools 100 are to be used. An exemplary material is Tyvek® available from DuPont. A label 332 may be affixed to or printed on the patch 330. The label 332 may include information such as a lot number and expiration date, for example.

Figure 10C:
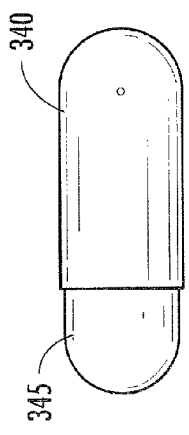
FIG. 10C is an enlarged view of an enclosure for enclosing the tools in the kit of FIG. 10B.

The tools 100 also may be enclosed in a cover before they are placed in the pouch 330. In the illustrated embodiment, a two-piece cover comprising a hollow tool cover 340 and a hollow tool tip cover 345 serves to enclose each tool 100. The two-piece cover may take the form of a capsule such that the two pieces can fit together and can be pulled apart. In this regard, as illustrated in FIG. 10C, the tool tip cover 345 may be press fit within the tool cover 340 to enclose the tool 100 before it is placed in the pouch 330. The tool cover 340 and tool tip cover 345 may then be pulled apart when the tool 100 is to be used. The tool cover 340 and tool tip cover 345 are preferably configured and sized to enclose the tool 100 and thereby inhibit puncturing of the pouch 330 by the tool 100. The tool cover 340 and tool tip cover 345 may be constructed of any material, such as a polymer, for example.

The pouch 310 including at least one patch 30 and/or the pouch 330 including at least one tool 100 may be commonly packaged in a pouch 320. The pouch 320 may be sealed closed and is preferably made of a strong material that is difficult to tear, but can be cut open when the patches 30 and/or the tools 100 are to be used. An exemplary material is Tyvek® available from DuPont. A label 322 may be affixed to or printed on the patch 320. The label 322 may include information such as the contents of the medical kit, a lot number, and expiration date, for example.

The kit 300 may also include other components described above, such as those components described above with regard to kit 200. Any additional component(s) may be packaged in their own pouch(es), and/or may be packaged in the general pouch 320.

The foregoing is illustrative of the present invention, and is not to be construed as limiting thereof. Although exemplary embodiments of this invention have been described, those skilled in the art will readily appreciate that many modifications are possible in the exemplary embodiments without materially departing from the novel teachings and advantages of this invention. As such, all such modifications are intended to be included within the scope of this invention. The scope of the invention is to be defined by the following claims.

That which is claimed is:

1. A surgical drape comprising:
   a surgical drape having first and second opposing primary surfaces; and
   at least one flexible patch having first and second opposing primary surfaces, wherein the at least one patch is fixably attached to one of the opposing primary surfaces of the surgical drape and overlies and covers at least a major portion of an aperture in the surgical drape, and wherein the at least one patch defines a through-port thereby allowing at least one cable, tool, or instrument to extend therethrough and through the surgical drape and be snugly held by the patch;
   wherein the at least one patch comprises a polymer with increased rigidity relative to an underlying portion of the surgical drape that the patch is attached to;
   wherein either the first or the second opposing primary surface of the at least one patch includes an adhesive to fixably attach the patch to one of the opposing primary surfaces of the surgical drape;
   wherein at least one of the opposing first and second primary surfaces of the at least one patch comprises a first inner portion and a second outer perimeter portion wherein only the second outer perimeter portion includes the adhesive.

2. The surgical drape according to claim 1, wherein the surgical drape is configured to attach to a magnet housing of a MRI system.

3. The surgical drape according to claim 2, wherein the at least one patch comprises at least two patches residing laterally spaced apart on the surgical drape for bilateral MRI procedures.

4. The surgical drape according to claim 1, wherein the at least one patch has an inner portion with a flexible material and a second material with increased structural rigidity relative to the inner portion that extends about a perimeter of the flexible material of the inner portion.

5. The surgical drape according to claim 1, wherein the surgical drape or the at least one patch includes a fold-over flap configured to overlay the at least one patch, wherein at least a portion of a periphery of the flap includes an adhesive layer such that the flap configured to adhesively attach to the cable, tool or instrument extending through the patch.

6. The surgical drape according to claim 1, wherein the at least one patch has a maximum thickness of between 1/20 to 1/2 of an inch.

7. The surgical drape according to claim 1, wherein the at least one patch has a first uninstalled configuration with a releasable cover overlying the adhesive and a second installed configuration whereby the patch resides on the surgical drape.

8. The surgical drape according to claim 1, wherein the at least one patch is scored to allow the at least one cable, tool or instrument to extend therethrough.

9. The surgical drape of claim 8, wherein the at least one patch has a closed surface that covers the aperture in the surgical drape when an object is not extending through the through-port.

10. The surgical drape of claim 1, wherein the through-port comprises a preexisting slit.

11. The surgical drape of claim 1, wherein the at least one patch comprises a unitary monolithic member.

12. The surgical drape of claim 11, wherein the through-port of the at least one patch comprises intersecting slits and has sufficient rigidity to support a cable extending therethrough.

13. The surgical drape of claim 12, wherein the through-port of the at least one patch comprises perpendicular slits that intersect and define four semi-rigid flaps.

14. The surgical drape of claim 1, wherein the through-port is configured to allow at least one cable to pass therethrough and clamp against the cable.

15. The surgical drape of claim 1, wherein the through-port comprises at least one slit defining a plurality of flexible flaps, wherein the flaps cooperate and contact an outer surface of the at least one cable, tool, or instrument as it extends through the through-port.

16. A surgical drape comprising:
   a surgical drape having first and second opposing primary surfaces; and
   at least one flexible patch having first and second opposing primary surfaces, wherein the at least one patch is fixably attached to one of the opposing primary surfaces of the surgical drape and overlies and covers at least a major portion of an aperture in the surgical drape, wherein the at least one patch includes a through-port comprising at least one slit, wherein the at least one patch is configured to allow at least one cable to extend through the through-port and the surgical drape and clamp the at least one cable in place;

wherein the at least one patch comprises a unitary monolithic polymer member with increased rigidity relative to an underlying portion of the surgical drape that the patch is attached to;

wherein either the first or the second opposing primary surface of the at least one patch includes an adhesive to fixably attach the patch to one of the opposing primary surfaces of the surgical drape;

wherein at least one of the opposing first and second primary surfaces of the at least one patch comprises a first inner portion and a second outer perimeter portion wherein only the second outer perimeter portion includes the adhesive.

* * * * *